United States Patent [19]

Hitney

[11] Patent Number: 5,327,359
[45] Date of Patent: Jul. 5, 1994

[54] METHOD AND SYSTEM FOR INFERRING THE RADIO REFRACTIVE INDEX STRUCTURE OF THE ATMOSPHERE FROM RADIO MEASUREMENTS

[75] Inventor: Herbert V. Hitney, San Diego, Calif.

[73] Assignee: The United States of America as represented by the Secretary of the Navy, Washington, D.C.

[21] Appl. No.: 950,569

[22] Filed: Sep. 24, 1992

[51] Int. Cl.$^5$ .............................................. G06F 15/20
[52] U.S. Cl. ................................... 364/550; 364/561; 364/562
[58] Field of Search .................. 342/26, 123; 364/550, 364/561, 562

[56] References Cited

U.S. PATENT DOCUMENTS 3,725,914  4/1973  Davidson et al. ..................... 342/26
4,125,893  11/1978  Hitney et al. ........................ 395/275

OTHER PUBLICATIONS

Hitney; "Remote Sensing of Refractivity Structure by Direct Radio Measurements at UHF"; Sep. 30, 1991-Oct. 4, 1991; pp. 1-5.

Primary Examiner—Edward R. Cosimano
Attorney, Agent, or Firm—Harvey Fendelman; Thomas Glenn Keough; Michael A. Kagan

[57] ABSTRACT

A system and method are provided for determining in real time, the radio refractive index structure of the atmosphere. The method may be characterized as comprising the steps of: transmitting a radio frequency signal over a predetermined path; receiving the radio frequency signal; detecting the strength of the radio frequency signal; determining a radio propagation factor from the strength of the radio frequency signal; determining a base height function of the atmosphere; and employing the radio propagation factor in the base height function to determine a trapping layer base height of the atmosphere which represents the radio refractive index structure of the atmosphere.

11 Claims, 2 Drawing Sheets

METHOD AND SYSTEM FOR INFERRING THE RADIO REFRACTIVE INDEX STRUCTURE OF THE ATMOSPHERE FROM RADIO MEASUREMENTS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates to a method for determining the radio refractive index ("RRI") structure of the atmosphere, and more particularly, to a method for determining the RRI structure of the atmosphere by detecting the strength of a radio frequency (RF) signal propagated over a predetermined path.

The radio refractive index of a medium such as the atmosphere is defined as $n = c/v$, where c is the speed of light in a vacuum and v is the speed of a radio wave in the medium. A typical value of n for air at the earth's surface is 1.000340. In the radio-wave propagation field, a dimensionless quantity, M, called the modified refractivity is defined as $M = [n - 1 + h/a] \times 10^6$, where h is the height above the surface of the earth and a is the radius of the earth. In the example given above, where $n = 1.000340$ and $h = 0$, $M = 340$. However, it is not the numeric value of M which is important, but rather the change in M as a function of a change in altitude which determines the characteristic of the radio refractive index structure that bears on the prediction of radio wave propagation through the atmosphere. The relation of M as a function of height describes the vertical RRI structure of the atmosphere at a particular location.

The vertical characteristics of the radio refractive index structure of the atmosphere influence the propagation of radio waves over a large range of frequencies by causing the path of the radio waves to bend or refract as they pass through adjacent layers of the atmosphere. It is important to know the radio refractive index structure of the atmosphere in order to predict the performance of a wide variety of radio equipment. An example of a system that uses the radio refractive index structure for such purposes is given in U.S. Pat. No. 4,125,893 entitled "Integrated Refractive Effects Prediction System," incorporated herein by reference.

Present methods for determining the vertical structure of the radio refractive index generally require direct measurement of atmospheric properties at various altitudes. Examples of systems deployed to make such direct measurements include balloon-borne radiosondes that measure pressure, temperature, and humidity, and also include aircraft-mounted refractometers that measure the radio refractive index and altitude. However, all direct sensing methods have the disadvantages of being expensive, logistically complex, and incapable of providing a real time determination of the radio refractive index structure.

Referring now to FIG. 1, there is shown an example of a modified refractivity versus height profile 10, represented by a solid line. Data used to construct the modified refractivity profile 10, presented by way of example in FIG. 1, were derived from radiosonde measurements taken off the coast of the Point Loma area of San Diego, California. The profile 10 is ideally approximated by three linear and serially connected segments 12, 14, and 16, shown as dashed lines which together idealize the modified refractivity versus height profile 10 (the segment 14 and the profile 10 are substantially coincident).

Each of the segments 12, 14, and 16 represent successive layers of the atmosphere, where each layer is characterized as having a modified refractivity which varies linearly with altitude. For example, the layer 12 represents the modified refractivity of a layer of the atmosphere adjacent to the earth having a radio refractive index which increases linearly with increasing altitude up to an altitude referred to as the trapping layer base height. The segment 14 represents the modified refractivity of a second layer of the atmosphere which is coterminous with the first layer at the trapping layer base height. However, the modified refractivity of the second layer decreases linearly with increasing altitude starting from the maximum modified refractivity of the first layer. The segment 16 represents the modified refractivity of a third layer of the atmosphere which increases linearly with increasing altitude starting from the minimum modified refractivity of the second layer.

Five modified refractivity parameters are used to construct the three segments 12, 14, and 16 which represent the RRI structure of the atmosphere. These refractivity parameters are: 1) an M-unit versus height gradient (slope) of the lowest segment 12; 2) an M-unit versus height gradient of the highest segment 16; 3) a total M-unit excursion, where the M-unit excursion represents the difference of M between the maximum and minimum altitude, $M_{14}$ of the second segment 14; 4) a vertical thickness, $h_{14}$, of the second segment 14; 5) and a height z of the base of the second segment 14, which is usually the height of the base of a temperature inversion layer, also referred to as the trapping layer base height. Of the five parameters, the trapping layer base height is the dominant factor for influencing many propagation effects. The radio refractive index structure for the San Diego, CA example is shown in FIG. 1 to have a trapping layer base layer height of about 620 meters.

Thus, it may be appreciated that a need exists for a system and method for readily determining the radio refractive index structure of the atmosphere, and more particularly, for determining the base height of a temperature inversion layer in real-rime.

SUMMARY OF THE INVENTION

Figure 1:
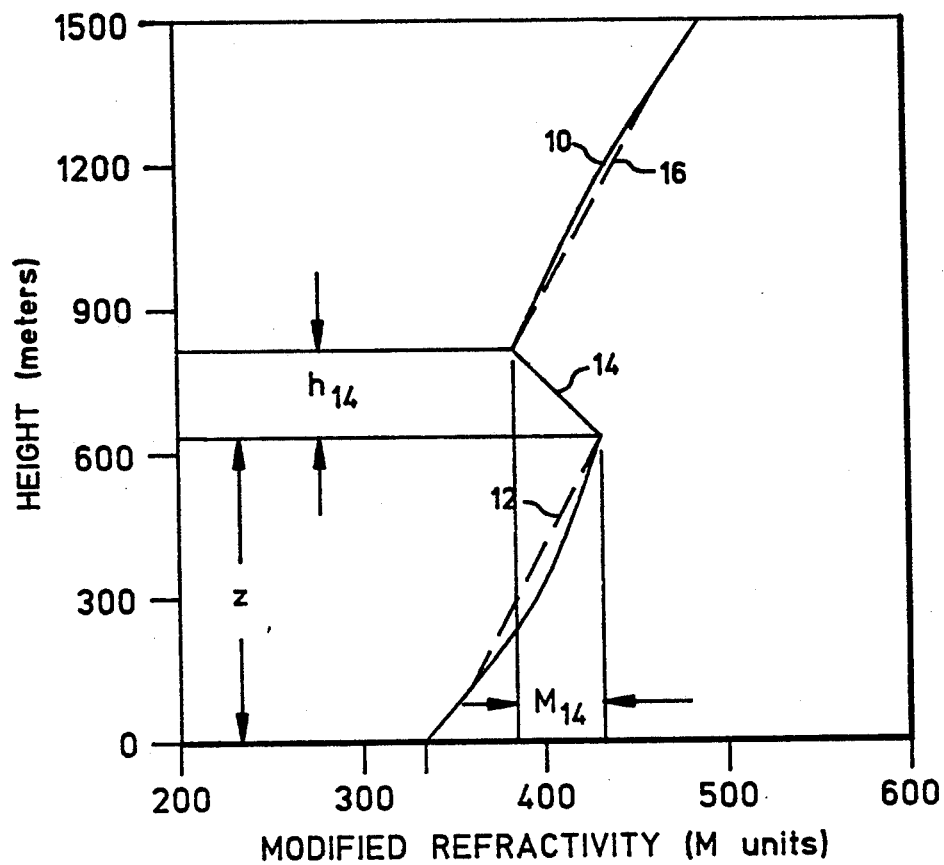
FIG. 1 presents an example of a radiosonde derived refractivity profile of the atmosphere off the coast of the Point Loma area of San Diego, California.

The present invention provides a system and method for determining in real time, the radio refractive index structure of the atmosphere. The method may be characterized as comprising the steps of: transmitting a radio frequency signal over a predetermined path; receiving said radio frequency signal; detecting the strength of said radio frequency signal; determining a radio propagation factor from said strength of said radio frequency signal; determining a base height function of the atmosphere; and employing said radio propagation factor in said base height function to determine a trapping layer base height of the atmosphere which represents said radio refractive index structure of the atmosphere.

A system embodying various features of the present invention comprises a radio frequency transmitter system for generating a radio frequency signal; a radio receiver system for detecting said radio frequency signal and generating a first output signal representing the strength of said detected radio signal; and a computer operably coupled to receive said first output signal for determining a radio propagation factor from said first output signal and for employing said radio propagation factor in a base height function to determine a trapping layer base height of the atmosphere representing said radio refractive index structure of the atmosphere, and generating a second output signal corresponding to aid trapping layer base height. The computer then may generate digital data representations of the radio refractive index structure based on the inferred trapping layer base height and long term statistics for the other modified refractivity parameters, described above.

DESCRIPTION OF THE PREFERRED EMBODIMENT

The present invention provides a system and method for ascertaining the radio refractive index structure of the lower atmosphere by determining the trapping layer base height of the atmosphere above a specific region of the surface of the earth. The method of the present invention is generally described in Hitney, H.V., "Remote Sensing of Refractivity Structure By Direct Radio Measurements At UHF," *AGARD 49th Symposium, Remote Sensing of the Propagation Environment,* 30 Sept.-4 October 1991, Cesme, Turkey. The invention provides an inexpensive method for inferring the radio refractive index structure of the atmosphere in real time using indirect measurement techniques, thereby avoiding the need for expensive and logistically complicated direct measurement techniques. Real time determination of the RRI structure may be employed to substantially improve the accuracy of predictions of radio equipment performance in comparison to predictions based on direct-measurement methods which only make measurements between relatively long time intervals and at only one location. The method may also be used to determine the average structure of the radio refractive index over a long path through the atmosphere, whereas standard techniques only provide the radio refractive index structure for one location. For many applications, determination of the average RRI structure would result in better predictions of RF system performance than predictions based on determination of just one structure near or along the RF propagation path.

Figure 2:
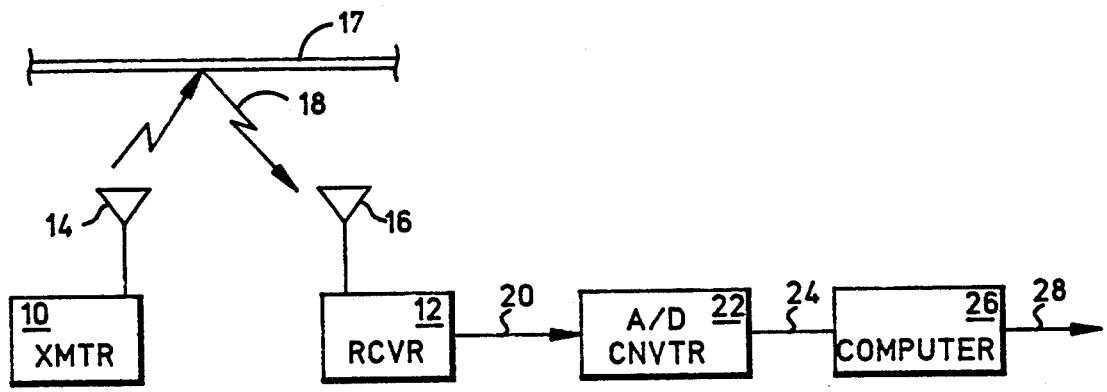
FIG. 2 is a block diagram of an example of a system embodying various features of the present invention which may be employed to determine the trapping layer base height of the atmosphere.

Referring to FIG. 2, the method of the invention involves establishing an RF propagation path between a transmitter 10 and receiver 12 in the area of interest. The transmitter 10 and receiver 12 are each coupled to an antenna 14 and antenna 16, respectively. The heights of the antennas are preferably less than about 50 meters above sea level, and more preferably, 30 meters or less, since the method works best when the antenna heights are below the RRI structure 17 being sensed. Various frequencies and path lengths appropriate for the requirements of a particular application may be used. The transmitter 10 generates an RF signal 18 which is detected by the receiver 12. The strength of the RF signal 18 as detected by the receiver 12 is compared to the theoretical strength such detected signal would have if propagated the same distance as between the transmitter 12 and receiver 14 through free space (the "free space signal strength"). The result of this comparison is referred to as a radio propagation factor. The radio propagation factor, preferably having the units of dB, results from taking the difference (in dB) between the free space signal strength and the strength of the detected signal 18. In response to detecting the RF signal 18, the receiver 12 generates an output signal 20 corresponding to the strength of the propagation factor. The output signal 20 is suitably conditioned by a n analog-to-digital converter 22 which provides a suitably conditioned digital signal 24 which is used as the variable input to an algorithm of a base height function implemented in a computer 26. The base height function determines a base height for a particular value of the propagation factor. The value of the base height for a particular propagation factor may be used as the input to another processing routine or may be provided to another device, such as a display, strip chart recorder, plotter, or computer.

Determining the base height function involves obtaining the long-term refractivity statistics for a geographical area of interest for which the refractive index structure of the atmosphere is desired. These statistics include the temperature, pressure, and humidity of the atmosphere at different altitudes above the surface of the earth. Such statistics may be obtained from data collected by multiple, routine radiosonde measurements and stored at the National Climatic Data Center, Ashville, NC (NOAA Products and Services, U.S. Government Printing Office, Washington, D.C. 20402, Stock No. 003-017-00413-9 . The long-term refractivity statistics are used to derive the five modified refractivity statistics described above. Techniques for deriving modified refractivity statistics from meteorological data are well known and are described in Bean, B.R., and Dutton, E.J., *Radio Meteorology,* Dover Publications, Inc., New York, New York, 1968, Chapter 1, page 7.

The modified refractivity statistics for the selected geographical area are provided as input to a suitable radio propagation model, i.e., one that correctly accounts for the radio refractive effects associated with the trapping layers. The radio propagation model is preferably incorporated into an appropriate processing routine implemented in a computer, or digital data processor which uses the long-term refractivity statistics to compute a unique value of the trapping layer base height for each different value of the propagation factor over the selected RF path. An example of a suitable radio propagation model for use in 19 conjunction with the present invention is described in U.S. patent application Ser. No. 07/834,916, filed Feb. 12, 1992, entitled "High Speed Method For Predicting Radio-Wave Propagation," now U.S. Pat. No. 5,301,127 incorporated herein by reference. By way of example, another suitable propagation model, which is preferably implemented in software, is the PCPEM (Personal Computer Parabolic Equation Model), published by Signal Science Limited, 20 Alexander Close, Abingdon OX14 1XA, United Kingdom.

Figure 3:
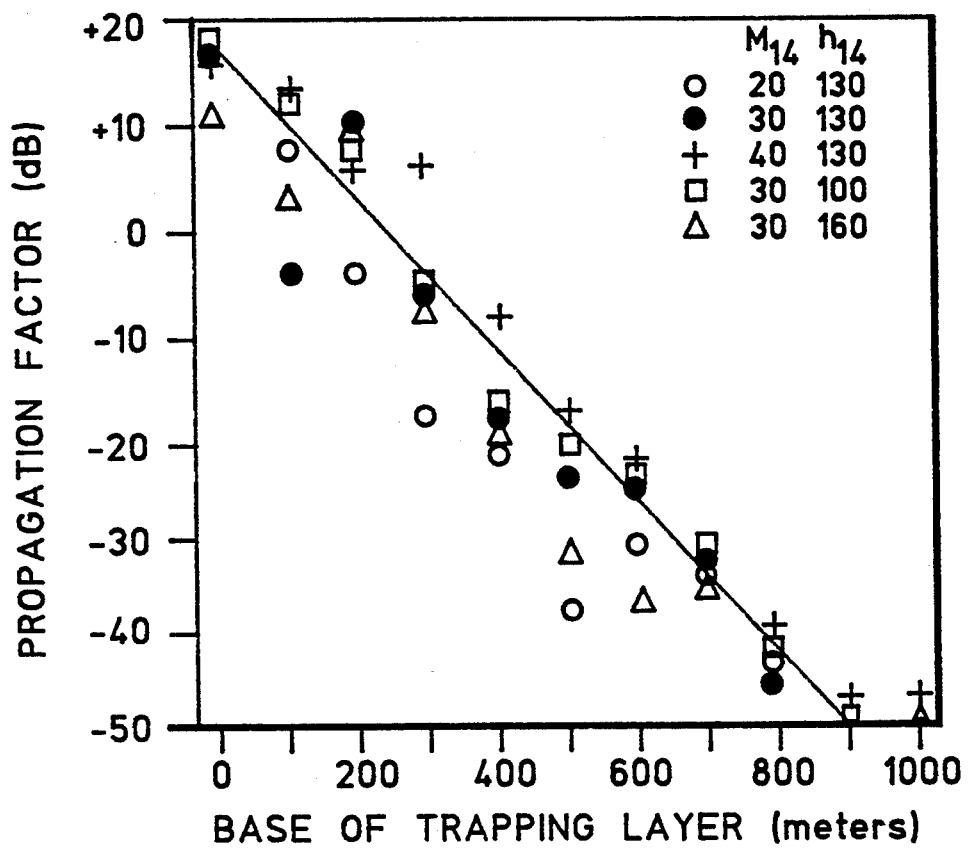
FIG. 3 is a graph illustrating a linear relationship between the propagation factor and the trapping layer base height.

The output of the radio propagation model is a set of ordered pairs, (f,z), where z is the desired base height in meters, and f is the propagation factor in dB representing the radio propagation factor, or predicted received strength of the RF signal 18. Conventional regression techniques may be used to derive a relationship between the radio propagation factor and the trapping layer base height in the region through which the radio signal 18 propagates. Such a relationship is illustrated, by way of example, in FIG. 3 as a linear function having a negative slope for the refractivity data of the Southern California area. Such linear relationship was derived by applying a straight line approximation to fit the data, giving preference to the median data set indicated by the solid circles. However, an algorithm using a least-squares fit may also be applied to relate a unique value of z for each unique value of f. For example, a linear base height function relating the propagation factor and trapping layer base height for the data presented in FIG. 3 may be approximated as:

$$z = 13.5 (16.6 - f).$$

As an alternative to employing a linear functional relationship between z and f, quadratic, cubic, polynomial, logarithmic, or other suitable mathematical relations may also be used, as would be well known by those of ordinary skill in the art. A suitable processing routine running in a digital computer may be employed to derive an algorithm of a functional relationship between the trapping layer base height and the propagation factor in accordance with techniques well known by those of ordinary skill in the art. Once the base height function is determined, such function may be easily embodied in a suitable processing software routine that may be implemented on the digital computer 26 whereby the propagation factor is used as the variable input to the base height function by which the trapping layer base height is determined.

The process of transmitting and detecting the strength of the RF signal propagated over the selected path, detecting the signal strength of the received RF signal, and then determining the trapping layer base height in the computer may be repeated so as to provide real time monitoring of the radio refractive index structure of the atmosphere over a period of time.

Obviously, many modifications and variations of the present invention are possible in light of the above teachings. It is therefore to be understood that within the scope of the appended claims, the invention may be practiced otherwise than as specifically described.

What is claimed is:

1. A method for determining the radio refractive index structure of the atmosphere comprising the steps of:
   transmitting a radio frequency signal over a predetermined path;
   receiving said radio frequency signal;
   detecting the strength of said radio frequency signal;
   determining a radio propagation factor from said strength of said radio frequency signal;
   determining a base height function of the atmosphere; and
   employing said radio propagation factor in said base height function to determine a trapping layer base height of the atmosphere which represents said radio refractive index structure of the atmosphere.

2. The method of claim 1 further including the step of determining said base height function for a particular region of interest.

3. The method of claim 2 further includes the step of relating modified refractivity characteristics of the atmosphere as a function of altitude.

4. The method of claim 3 wherein said radio frequency signal is transmitted and received at an altitude no greater than about 50 meters above sea level.

5. A method for determining the radio refractive index structure of the atmosphere comprising the steps of:
   transmitting a radio frequency signal over a predetermined path;
   receiving said radio frequency signal;
   detecting the strength of said radio frequency signal;
   determining a radio propagation factor from said strength of said radio frequency signal;
   determining a base height function of the atmosphere for a particular region of interest using a radio propagation model;
   employing said radio propagation factor in said base height function to determine a trapping layer base height of the atmosphere representing said radio refractive index structure of the atmosphere.

6. The method of claim 5 wherein said radio frequency signal is transmitted and received at an altitude no greater than about 50 meters above sea level.

7. A system for inferring the radio refractive index structure of the atmosphere, comprising:
   a radio frequency transmitter system for generating a radio frequency signal;
   a radio receiver system for detecting said radio frequency signal and generating a first output signal representing the strength of said detected radio signal; and
   a computer operably coupled to receive aid first output signal for determining a radio propagation factor from said first output signal and for employing said radio propagation factor in a base height function to determine a trapping layer base height of the atmosphere representing said radio refractive index structure of the atmosphere, and generating a second output signal corresponding to said trapping layer base height.

8. The system of claim 7 wherein said base height function includes a radio propagation model.

9. The system of claim 8 wherein said base height function is derived using long term refractivity statistics for a geographical region of interest.

10. A system for determining the radio refractive index structure of the atmosphere, comprising:
    a transmitting system for transmitting a radio frequency signal over a predetermined path;
    a receiving system for receiving said radio frequency signal;
    computing means for detecting the strength of said radio frequency signal, determining a radio propagation factor from said strength of said radio frequency signal, using said radio propagation factor in an atmospheric base height function to determine a trapping layer base height of the atmosphere which represents said radio refractive index structure of the atmosphere.

11. The system of claim 10 wherein said atmospheric base height function includes a radio propagation model.

* * * * *